US012672833B2

(12) United States Patent
Inoue et al.

(10) Patent No.: US 12,672,833 B2
(45) Date of Patent: Jul. 7, 2026

(54) X-RAY CT APPARATUS, RADIATION DETECTING APPARATUS, AND DATA PROCESSING METHOD FOR X-RAY CT APPARATUS

(71) Applicant: CANON KABUSHIKI KAISHA, Tokyo (JP)

(72) Inventors: Motohiro Inoue, Otawara (JP); Hiroaki Miyazaki, Otawara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 86 days.

(21) Appl. No.: 18/596,843

(22) Filed: Mar. 6, 2024

(65) Prior Publication Data

US 2024/0298977 A1     Sep. 12, 2024

(30) Foreign Application Priority Data

Mar. 10, 2023     (JP) ................................. 2023-038064

(51) Int. Cl.
*A61B 6/03*          (2006.01)
*A61B 6/42*          (2024.01)
(52) U.S. Cl.
CPC ............ *A61B 6/032* (2013.01); *A61B 6/4233* (2013.01)
(58) Field of Classification Search
CPC ............................... A61B 6/032; A61B 6/4233
See application file for complete search history.

(56) References Cited

U.S. PATENT DOCUMENTS

| | | | |
|---|---|---|---|
| 2004/0114706 A1* | 6/2004 | Ikeda | ..................... A61B 6/032 |
| | | | 378/4 |
| 2009/0128216 A1 | 5/2009 | Rao et al. | |
| 2009/0129537 A1 | 5/2009 | Rao et al. | |
| 2009/0132789 A1 | 5/2009 | Rao et al. | |
| 2016/0033654 A1* | 2/2016 | Tamura | ................. G01T 1/2985 |
| | | | 378/98.9 |
| 2018/0132799 A1* | 5/2018 | Nakanishi | ............ A61B 6/5258 |

FOREIGN PATENT DOCUMENTS

| | | | |
|---|---|---|---|
| JP | 2012-511139 A | | 5/2012 |
| JP | 2012187180 A | * | 10/2012 |

* cited by examiner

*Primary Examiner* — Uzma Alam
*Assistant Examiner* — Fani Polyzos Boosalis
(74) *Attorney, Agent, or Firm* — Oblon, McClelland, Maier & Neustadt, L.L.P.

(57)          ABSTRACT

According to one embodiment, X-ray CT apparatus includes an X-ray tube, an energy integrating type detector, a time data generation circuit, and a projection data generation unit. The X-ray tube emits X-rays. The energy integrating type detector has a plurality of detector units arrayed in a channel direction that accumulate electric charges corresponding to X-rays transmitted through an object. The time data generation circuit generates time data at a timing when the electric charges accumulated in the detector reach a predetermined threshold. The projection data generation unit generates projection data using the time data and energy corresponding to the threshold.

12 Claims, 9 Drawing Sheets

AGGREGATED EVENT DATA

| | ch. 1 | ch. 2 | ch. 3 | ch. 4 | ch. 5 | ch. 6 | $\cdots$ | ch. M |
|---|---|---|---|---|---|---|---|---|
| $t_1$ | 1 | 1 | 0 | 1 | 1 | 1 | $\cdots$ | 1 |
| $t_2$ | 0 | 1 | 1 | 1 | 0 | 0 | $\cdots$ | 1 |
| $t_3$ | 1 | 1 | 0 | 0 | 0 | 1 | $\cdots$ | 0 |
| $t_4$ | 1 | 0 | 1 | 1 | 1 | 0 | $\cdots$ | 0 |
| $t_5$ | 0 | 0 | 0 | 0 | 1 | 0 | $\cdots$ | 0 |
| $t_6$ | 0 | 0 | 0 | 1 | 1 | 0 | $\cdots$ | 1 |
| $t_7$ | 1 | 1 | 0 | 0 | 0 | 0 | $\cdots$ | 1 |
| $t_8$ | 0 | 1 | 1 | 1 | 0 | 1 | $\cdots$ | 0 |
| $t_9$ | 0 | 0 | 0 | 0 | 0 | 1 | $\cdots$ | 1 |
| $t_{10}$ | 0 | 0 | 0 | 0 | 0 | 0 | $\cdots$ | 1 |
| $\vdots$ | $\vdots$ | $\vdots$ | $\vdots$ | $\vdots$ | $\vdots$ | $\vdots$ | $\cdots$ | $\vdots$ |
| $t_{N-2}$ | 0 | 1 | 0 | 0 | 0 | 0 | $\cdots$ | 0 |
| $t_{N-1}$ | 0 | 0 | 1 | 0 | 1 | 1 | $\cdots$ | 1 |
| $t_N$ | 1 | 1 | 1 | 1 | 0 | 1 | $\cdots$ | 0 |
| $t_1$ | 0 | 0 | 0 | 1 | 1 | 0 | $\cdots$ | 1 |
| $t_2$ | 1 | 1 | 1 | 0 | 0 | 0 | $\cdots$ | 1 |
| $t_3$ | 0 | 1 | 0 | 1 | 0 | 1 | $\cdots$ | 0 |
| $t_4$ | 1 | 0 | 0 | 1 | 1 | 0 | $\cdots$ | 0 |
| $t_5$ | 0 | 0 | 1 | 0 | 1 | 0 | $\cdots$ | 0 |
| $t_6$ | 0 | 0 | 0 | 0 | 0 | 1 | $\cdots$ | 1 |
| $t_7$ | 0 | 0 | 0 | 0 | 0 | 0 | $\cdots$ | 1 |
| $t_8$ | 1 | 1 | 0 | 1 | 1 | 1 | $\cdots$ | 1 |
| $t_9$ | 0 | 1 | 1 | 1 | 0 | 0 | $\cdots$ | 1 |
| $t_{10}$ | 1 | 1 | 0 | 0 | 0 | 1 | $\cdots$ | 0 |
| $\vdots$ | $\vdots$ | $\vdots$ | $\vdots$ | $\vdots$ | $\vdots$ | $\vdots$ | $\cdots$ | $\vdots$ |
| $t_{N-2}$ | 0 | 0 | 0 | 0 | 1 | 1 | $\cdots$ | 1 |
| $t_{N-1}$ | 1 | 1 | 1 | 1 | 0 | 1 | $\cdots$ | 0 |
| $t_N$ | 0 | 1 | 1 | 0 | 0 | 0 | $\cdots$ | 0 |

VIEW (n) — TIME

VIEW (n+1) — TIME

FIG. 6

AREA CORRESPONDING TO SECOND PROJECTION DATA
CALCULATED FROM SECOND EVENT DATA (NORMAL SPATIAL
RESOLUTION IS OBTAINED USING NORMAL VIEW RATE)

REGION CORRESPONDING TO FIRST PROJECTION
DATA CALCULATED FROM FIRST EVENT DATA
(UP-SAMPLING TO HIGHER VIEW RATE THAN NORMAL
VIEW RATE RESULTS IN HIGHER SPATIAL RESOLUTION)

X-RAY CT APPARATUS, RADIATION DETECTING APPARATUS, AND DATA PROCESSING METHOD FOR X-RAY CT APPARATUS

CROSS-REFERENCE TO RELATED APPLICATIONS

This application claims the benefit of priority of Japanese Patent Application No. 2023-038064, filed Mar. 10, 2023, the entire contents of which are incorporated herein by reference.

FIELD

Embodiments described herein relate generally to an X-ray CT apparatus, a radiation detecting apparatus, and a data processing method for X-ray CT apparatus.

BACKGROUND

An X-ray CT (Computed Tomography) apparatus is a medical imaging device that generates a tomographic image of an object based on X-rays detected by an X-ray detector by irradiating the object with X-rays. The X-ray CT apparatus collects a large number of projection data by continuously imaging the object while rotating a pair of X-ray tube and X-ray detector around the object at high speed, and generates a tomographic image by reconstructing the large number of projection data.

A large number of projection data are collected during one rotation of the X-ray tube and X-ray detector pair around the object. The projection data collected at each angle during one rotation is called a view. The number of views per unit time is called the view rate.

Generally, the higher the view rate, the higher the spatial resolution and the higher resolution tomographic image can be generated.

In the field of view (FOV), which is the region of the object to be imaged, the spatial resolution required is different between the center of the FOV and the edges of the FOV. The spatial resolution required also differs depending on the part of the region within the FOV and the nature of the specific region.

In conventional X-ray CT apparatus, the view rate is normally constant. By setting the view rate uniformly high, the spatial resolution can be increased, but the data volume also increases. As mentioned above, some regions of FOV of the object require high spatial resolution, while others do not. Therefore, the method of uniformly increasing the view rate is not rational because such method increases the amount of data that is not originally needed and thus places restrictions on the amount of data transmission.

BRIEF DESCRIPTION OF THE DRAWINGS

FIG. 6 is a diagram explaining an example of an aggregated event data.

FIG. 8 is a first diagram showing an example of processing for generating the first and second projection data from event data for transmission.

DETAILED DESCRIPTION

Hereinbelow, a description will be given of an X-ray CT apparatus, a radiation detecting apparatus, and a data processing method for X-ray CT apparatus according to embodiments of the present invention with reference to the drawings. In the following description, components having the same function and configuration are indicated with the same numerals, and duplicate explanations are given only when necessary.

In general, according to one embodiment, X-ray CT apparatus includes an X-ray tube, an energy integrating type detector, a time data generation circuit, and a projection data generation unit. The X-ray tube emits X-rays. The energy integrating type detector has a plurality of detector units arrayed in a channel direction that accumulate electric charges corresponding to X-rays transmitted through an object. The time data generation circuit generates time data at a timing when the electric charges accumulated in the detector reach a predetermined threshold. The projection data generation unit generates projection data using the time data and energy corresponding to the threshold.

Figure 1:
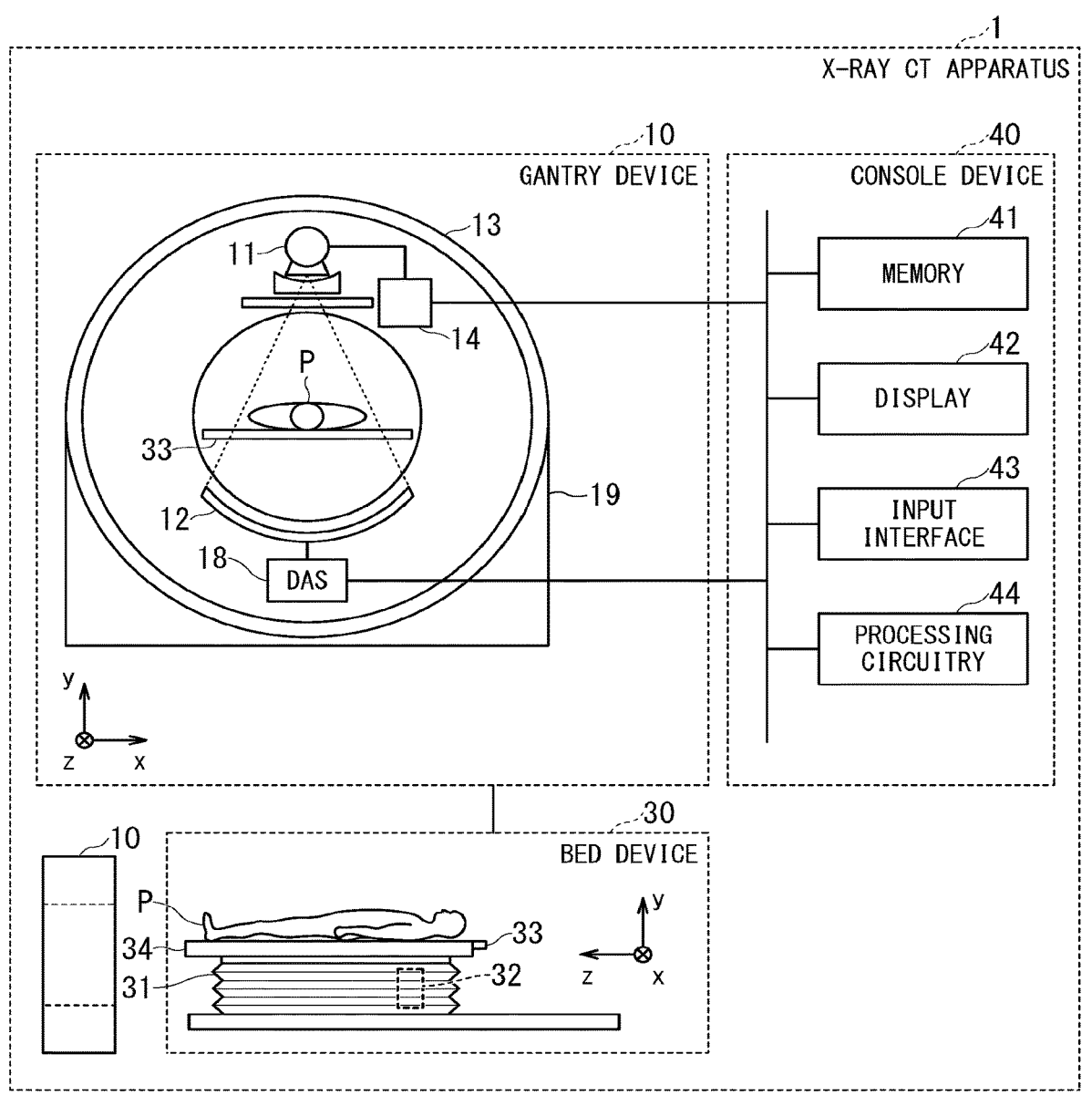
FIG. 1 is a schematic diagram showing an example configuration of an X-ray CT apparatus according to the present embodiment.

FIG. 1 is a schematic diagram showing an example configuration of an X-ray CT apparatus 1 according to the present embodiment. As shown in FIG. 1, the X-ray CT apparatus 1 has a gantry device 10, a bed device 30, and a console device 40. In FIG. 1, for convenience of explanation, a plurality of gantry devices 10 are shown on both the top and bottom left side in different orientations, but it refers to one gantry device 10 in actual configuration.

In FIG. 1, the longitudinal direction of tabletop 33 is defined as the z-axis direction, the axial direction orthogonal to the z-axis direction and parallel to the floor surface as the x-axis direction, and the axial direction orthogonal to the z-axis direction and vertical to the floor surface as the y-axis direction.

The bed device 30 has a base 31, a bed drive mechanism 32, a tabletop 33, and a support frame 34. An object P to be scanned is placed on the bed device 30. The base 31 is a housing that supports the support frame 34 in a vertical direction (y-axis direction). The tabletop 33 is a board on the top surface of the support frame 34 on which the object P is placed.

The bed drive mechanism 32 is a motor or actuator that moves the tabletop 33 on which the object P is placed under the control of the control device 15. The tabletop 33 can be moved in the longitudinal (z-axis) and vertical (y-axis) directions by the bed drive mechanism 32.

The gantry device 10 includes an X-ray tube 11, an X-ray detector 12, a rotating frame 13, an X-ray high voltage device 14, a gantry base 19, and a data acquisition system (DAS) 18. The X-ray tube 11, for example, receives a high-voltage power supply from the X-ray high-voltage device 14 and irradiates hot electrons from the filament toward the target.

The X-ray detector 12 has, for example, a row of X-ray detector elements in which a plurality of X-ray detector elements is arranged in the channel direction along a single arc centered at the focal point of the X-ray tube 11. The X-ray detector 12 detects the X-ray beam irradiated from the X-ray tube 11 and passing through the object P, converts the detected X-rays into electrical signals, and outputs the signals to the DAS 18.

The rotating frame 13 is freely supported for rotation with its center as the axis of rotation. The rotating frame 13 is driven under the control of the console device 40 and the like to rotate the X-ray tube 11 and X-ray detector 12 with respect to the gantry device 10 and bed device 30.

The X-ray high voltage device 14 includes a high voltage generator having a function of generating high voltage to be applied to the X-ray tube 11 and provided with an electric circuit such as a transformer. The X-ray high voltage device 14 also includes an X-ray control device that controls the output voltage according to the X-rays irradiated by the X-ray tube 11.

The gantry base 19 is a housing that supports the aperture of the gantry device 10 in the vertical direction (y-axis direction). The gantry base 19 may be provided with a gantry tilt mechanism that allows the aperture of the gantry base 19 facing the bed device 30 to be tilted forward or backward with respective to the vertical direction (y-axis direction).

The DAS (Data Acquisition System) 18 generates event data by performing the processing described below on the electrical signals output from each X-ray detector element of X-ray detector 12, and transmits the generated event data to console device 40. The detailed configuration and operation of the DAS 18 will be described below.

The console device 40 includes a memory 41, a display 42, an input interface 43, and processing circuitry 44.

The memory 41 stores various processing programs used in the processing circuitry 44, various data necessary to execute the programs, and image data such as tomographic images generated by the processing circuitry 44. The memory 41 has a configuration that includes a magnetic or optical storage medium, or a semiconductor memory or other storage medium that can be read by the processor.

The processing circuitry 44 is a dedicated or general-purpose processor that performs various functions described below by executing a program stored in the memory 41. Here, the term processor includes, for example, dedicated or general-purpose CPU (Central Processing Unit) as well as GPU (Graphics Processing Unit) and other processors.

The processing circuitry 44 includes application-specific integrated circuits (ASICs), programmable logic devices (e.g., Simple Programmable Logic Device (SPLD), Complex Programmable Logic Device (CPLD), or Field Programmable Gate Array (FPGA)). When the processing circuitry 44 is composed of an ASIC, for example, instead of storing the program in the memory 41, the functions corresponding to the program are directly incorporated into the ASIC as logic circuits. The processing circuitry 44 can also realize various functions by combining software processing using a processor and hardware processing using hardware elements such as an ASIC.

When the processing circuitry 44 is composed of processors, each function may be realized by a single processor, or multiple independent processors may be combined to form the processing circuitry, and each processor may realize each function. When multiple processors are provided, the memory 41 that stores the program may be provided separately for each processor, or a single memory 41 may store the programs corresponding to the functions of all processors at once.

Figure 2:
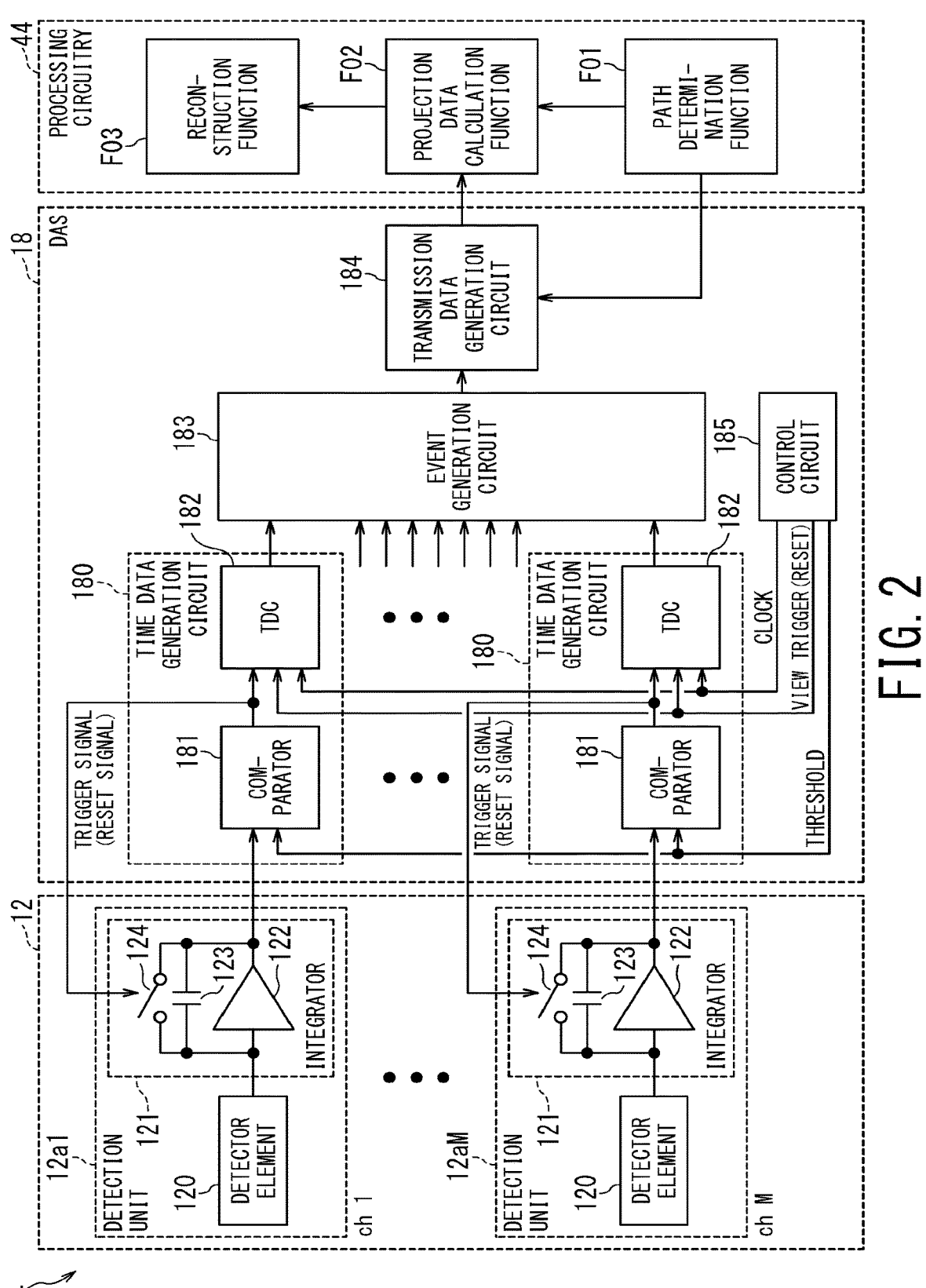
FIG. 2 is a block diagram showing a detailed configuration and functions of a detector, DAS, and processing circuitry of a console.

FIG. 2 is a block diagram showing more detailed configuration and functions of the detector 12, the DAS 18, and the processing circuitry 44 according to the present embodiment shown in FIG. 1.

As mentioned above, the X-ray CT apparatus 1 includes a plurality of detector units 12a arranged along an arc centered at the focal point of the X-ray tube 11. When the number of detector units 12a is M, the X-ray CT apparatus 1 includes M detector units 12al to 12aM, and these are collectively referred to as detector units 12a. The direction of arrangement of the multiple detector units 12a along the arc is called the channel direction, and each of the multiple detector units 12a can be identified by a channel number. For example, the X-ray CT apparatus 1 is composed of M detector units 12a from channel 1 (ch 1) to channel M (ch M), as illustrated in FIG. 2.

The plurality of detector units 12a may be arranged in two dimensions in the channel direction and in the slice direction (Z-axis direction in FIG. 1). The slice direction isss orthogonal to the channel direction.

Each detector unit 12a is configured as an energy integrating type detector that accumulates electric charges according to the X-rays transmitted through the object. More specifically, each of the plurality of detector units 12a comprises a detector element 120 and an integrator 121. The detector element 120, for example, detects light converted from X-rays and outputs electric charges corresponding to the X-rays transmitted through the object to the integrator 121.

The integrator 121 integrates (i.e., accumulates) the electric charges output from the detector element 120. The configuration of the integrator 121 is not particularly limited. The integrator 121 may include, for example, an operational amplifier 122 and a capacitor 123, as illustrated in FIG. 2. The integrator 121 may also include a reset switch 124 for resetting the charge stored in the capacitor 123.

The DAS 18 has a plurality of time data generation circuits 180 corresponding to the plurality of detector units 12a, an event generation circuit 183, a transmission data generation circuit 184, and a control circuit 185.

The time data generation circuit 180 generates time data at the timing when the electric charge accumulated in the detector unit 12a reaches a predetermined threshold. For example, each of the time data generation circuits 180 includes a comparator 181 and a TDC (Time to Digital Converter).

The comparator 181 generates a trigger signal when the electric charge accumulated in the detector unit 12a exceeds the predetermined threshold. The generated trigger signal is used to reset the charge stored in the detector unit 12a. Specifically, the trigger signal is sent to the integrator 121 of the detector unit 12a to reset the charge stored in the capacitor 123 by closing the reset switch 124 of the integrator 121.

The threshold used for threshold determination in the comparator 181 is, for example, sent from the control circuit 185 provided in the DAS 18. The threshold may be pre-stored in a memory inside the control circuit 185, or may be configured so as to be able to be changed externally, such as by the console device 40.

The TDC 182 is a device that converts the input time of an electrical pulse signal into time data as a digital quantity. In the present embodiment, the TDC 182 is input (receives) the trigger signal generated by the comparator 181 and generates time data at the timing when the trigger signal is input.

In addition to the trigger signal, a clock signal and a view trigger as a reset signal, for example, are input to the TDC 182. The clock cycle of the clock signal defines the minimum unit of time data. The count-up value of the time data is reset to zero by the view trigger. The detailed operation of the comparator 181 and the TDC 182 will be described below.

The event generation circuit 183 generates event data related to an event. An "event" in the embodiment refers to an event indicating that the electric charge accumulated in each of the detector units 12a has reached the predetermined threshold. And "event data" in the embodiment refers to a data set where a time data indicating the time when the event occurred is associated with channel identification information such as the channel number of the detector unit 12a where the event occurred. Specific examples of event data will be described below.

The transmission data generation circuit 184 makes event data for the first path to be the first event data having the frequency of occurrence of the events maintained at the first view rate. The transmission data generation circuit 184 generates the second event data as the event data for the second path by aggregating the event occurrences and reducing the frequency of event occurrence such that the frequency of event occurrences after aggregation is at a second view rate lower than the first view rate. The transmission data generation circuit 184 generates event data for transmission by combining the first event data and the second event data.

The first view rate of the first event data described above is a view rate with a resolution adapted to minute angle. The minute angle is obtained by dividing a predetermined view interval, e.g., the normal view interval, that is, the angle between adjacent normal views, into multiple portions. The second view rate of the second event data described above is a view rate that is reduced from the first view rate by accumulating the number of events in the event data corresponding to the second path for each predetermined view, i.e., each normal view.

The view rate is the number of views per unit time, as described above, and can also be referred to as the number of views per unit angle by replacing the rotation time of the X-ray tube 11 and the detector 12 with the rotation angle. A view is the data set, i.e., projection data, collected by detector 12 in one angular direction during the rotation of the X-ray tube 11 and the detector 12.

In this specification, when simply referring to a "view", it means "a view with a normal view rate". Also, when "normal" view rate, "normal" spatial resolution, and "normal" view interval are described herein, they refer to the view rate, spatial resolution, and view interval, respectively, in the conventional X-ray CT apparatus without the up-sampling process which uses time data implemented by the X-ray CT apparatus 1 according to the present embodiment.

The first path described above refers to the path where, when the X-ray tube 11 and the detector 12 rotate, the X-ray emitted from the X-ray tube 11 passes through the determined region set in the FOV (Field of View) of the object and enters the detector 12. The second path is the path where the X-ray emitted from the X-ray tube 11 enters the detector without passing through the determined region.

The processes related to setting the determined region and identifying the first and second paths are performed, for example, by the path determination function F01 executed by the processing circuitry 44 in the console device 40.

The processing circuitry 44 realizes functions including the path determination function F01, the projection data calculation function F02, and the reconstruction function F03.

Based on the first event data described above, the projection data calculation function F02 generates the first projection data that is upsampled to a first view rate higher than the second view rate which is a predetermined view rate (e.g., the conventional normal view rate). For example, with respect to the first event data described above, the projection data calculation function F02 divides the energy corresponding to the threshold by the interval between the time data of two adjacent events, so as to generate the first projection data where the projection data of the first path passing through the determined region is upsampled to the first view rate adapted to the minute angle The projection data calculation function F02 also generates, with respect to the second event data, second projection data having a second view rate corresponding to the normal view rate based on the aggregation of the number or events.

The reconstruction function F03 generates a two dimensional or three dimensional CT image by applying reconstruction processing using the back projection method or the like to the first projection data and the second projection data.

Figure 3:
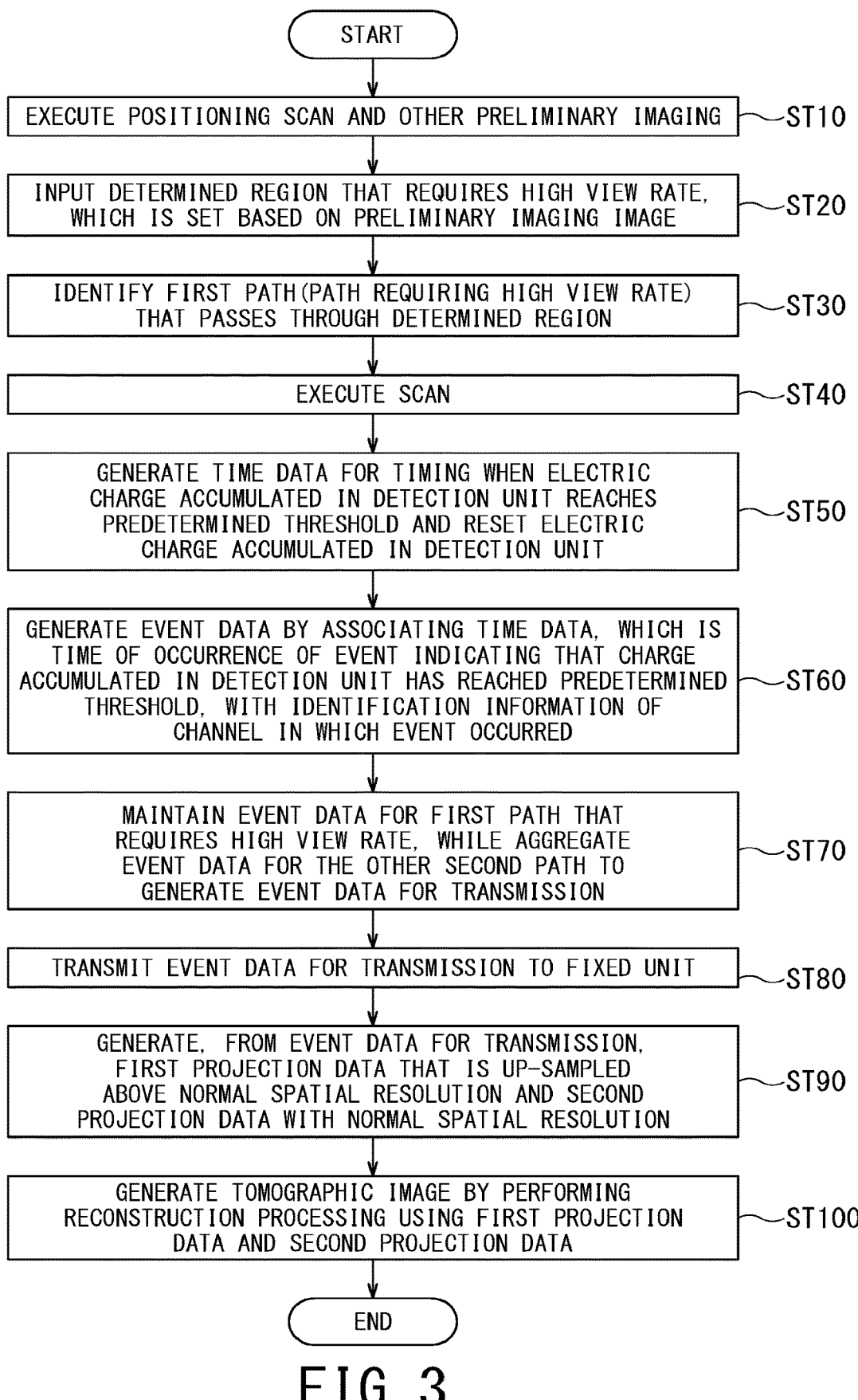
FIG. 3 is a flowchart showing an example of an operation of the X-ray CT apparatus according to the present embodiment.

FIG. 3 is a flowchart showing an example of the operation of the X-ray CT apparatus 1 according to the present embodiment. Hereinafter, the flowchart and the illustrations from FIG. 4 to FIG. 9 will be used to explain more specific examples of the operation of the X-ray CT apparatus 1.

First, at step ST10 in FIG. 3, preliminary imaging such as a positioning scan is performed using, for example, the X-ray CT apparatus 1. Then, the image generated by the preliminary imaging (hereinafter referred to as preliminary imaging image) is displayed on the display 42 of the X-ray CT apparatus 1, for example.

The preliminary imaging image displayed on the display 42 is evaluated by a user such as a physician or radiographer, and a determined region is set by the user within the FOV (Field of View) of the object's main imaging area. The determined region in the embodiment is a region set as a region where a higher resolution than the normal spatial resolution is necessary or desirable.

In step ST20, information about the determined region set by the user, i.e., the region where a high view rate is necessary or desirable, is input.

In step ST30, a first path, i.e., a path that requires a high view rate, through the determined region is identified. The paths other than the first path are the second paths that do not pass through the determined region and do not necessarily require a high view rate. Steps ST20 and ST30 are performed by the path determination function F01 of the processing circuitry 44.

Figure 4:
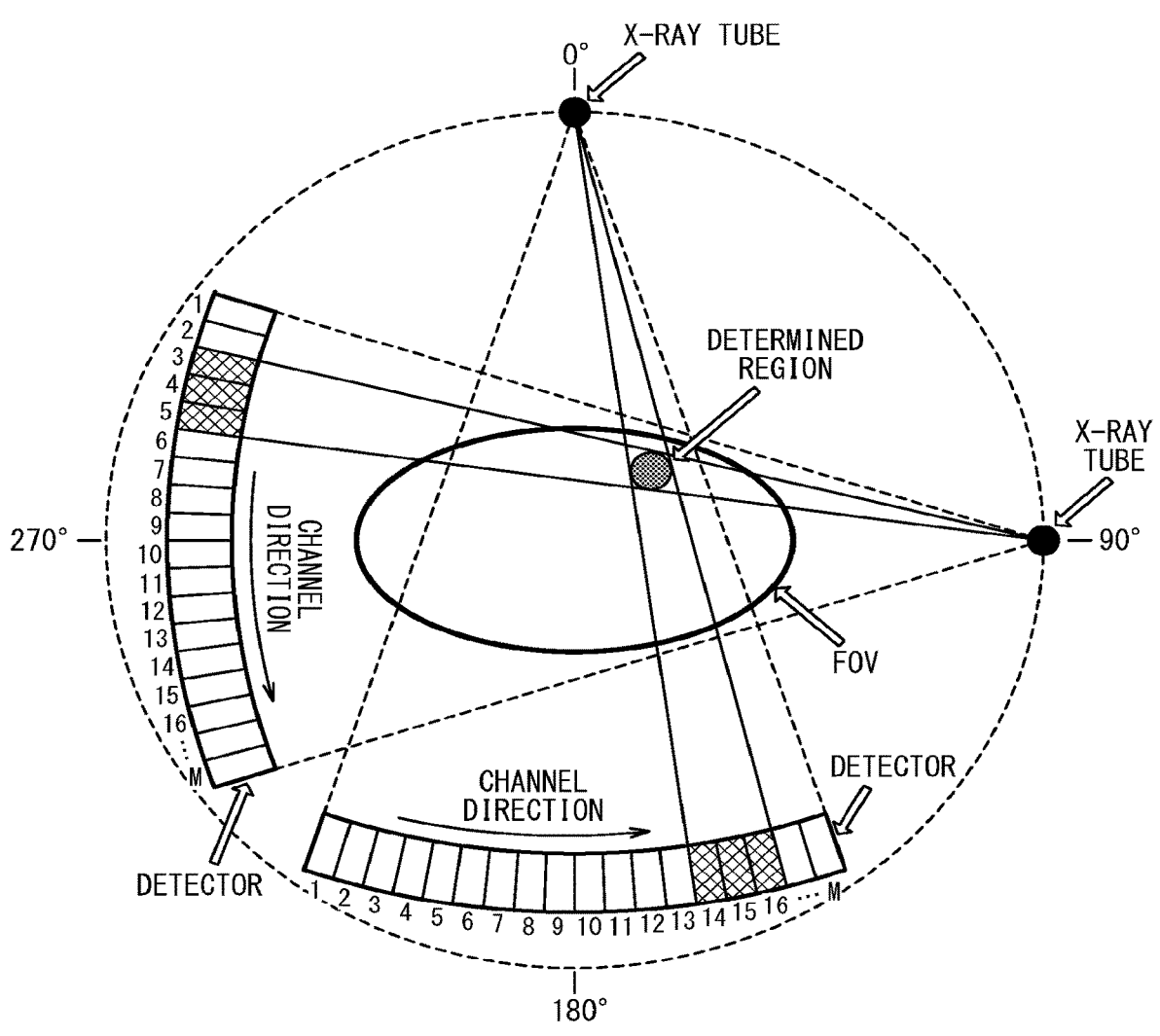
FIG. 4 is an explanatory diagram illustrating a concept of a determined region and the first and second paths.

FIG. 4 is an explanatory diagram illustrating the concept of the processing of steps ST20 and ST30. As shown in FIG.

4, in step ST20, a determined region is set within the FOV, which is the imaging area of the object to be imaged in the main scan.

Here, the determined region is, for example, at least one of (a) a peripheral region of the FOV, (b) a region with microstructure that is determined, based on a preliminary imaging image of the object, to be prone to partial volume effects, and (c) a region in the vicinity of dense material that is determined, based on a preliminary imaging image of the object, to be prone to artifacts.

Generally, the peripheral regions of the FOV have lower spatial resolution than the central region of the FOV. Therefore, by increasing the spatial resolution of the peripheral regions of the FOV, the entire FOV can be made more uniform in spatial resolution.

The partial volume effect means that when a plurality of tissues exists within a voxel, the pixel value represents the average value of the plurality of tissues. The partial volume effect makes it difficult to separate fine structures, but by increasing the spatial resolution, the partial volume effect can be suppressed and fine structures can be isolated.

In addition, by increasing the spatial resolution of the area around the dense material, artifacts caused by the dense material can be suppressed.

Spatial resolution can also be expressed as spatial frequency, and in particular, spatial resolution in the X-ray CT apparatus 1 can also be expressed as view rate.

In step ST30, for each view (in other words, for each rotation angle corresponding to each view), the first path and the second path are identified.

For example, in a view with a rotation angle of 0 degrees for the X-ray tube 11, the path from the X-ray tube 11 to the three detector units 12a of channels 14, 15, and 16 (detector unit 12a indicated by hatching) is identified as the first path, and the paths to other detector units 12a than the first path are identified as the second path.

In a view with a rotation angle of 90 degrees for the X-ray tube 11, the path from the X-ray tube 11 to the three detector units 12a of channels 3, 4, and 5 (detector unit 12a indicated by hatching) is identified as the first path, and the paths to other detector units 12a than the first path are identified as the second path.

In FIG. 4, only two views where rotation angles of the X-ray tube 11 being 0 and 90 degrees are shown as examples to avoid complication, but in reality, the first and second paths are identified for all views with a rotation angle of 360 degrees.

The first and second paths identified for each view as described above are temporarily stored in the appropriate memory.

Returning to FIG. 3, in step ST40, the main scan is performed for the main imaging. The processes from step ST50 to step ST90 are performed during the main scan.

In step ST50, the time data at the timing when the electric charges accumulated in detector unit 12a reaches the predetermined threshold is generated, and the electric charges accumulated in the detector unit 12a is reset.

In step ST60, event data is generated by associating the time data, which is the time of occurrence of the event indicating that the electric charges accumulated in the detector unit 12a has reached the predetermined threshold, with the identification information of the channel where the event occurred. In other words, in step ST60, event data is generated by associating the time data indicating the time at which the event occurred with the identification information of the detector unit 12a in which the event occurred.

Figure 5:
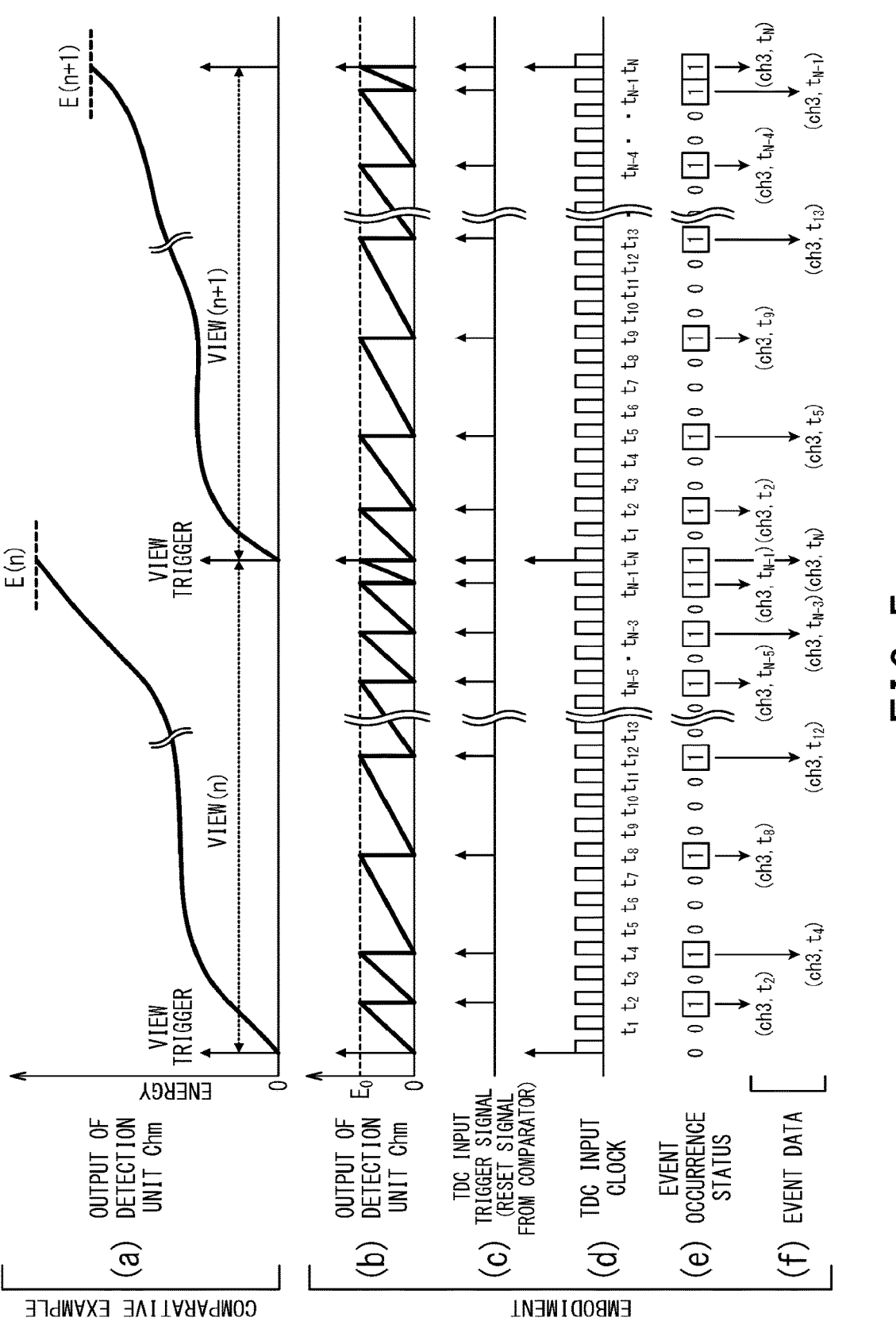
FIG. 5 is a timing chart explaining an operation from an output of the detector to a generation of event data in the X-ray CT apparatus according to the present embodiment.

FIG. 5 and FIG. 6 illustrate the processing concept of step ST50 and step ST60.

The part (a) in FIG. 5 is a timing chart showing an example of the output signal of a conventional energy integrating type detector as a comparative example to the present embodiment. For example, the output signal of the detector unit with channel number m (chm) accumulates charge immediately after the view trigger generated at the switching timing between views, resets the charge at the next view trigger, and repeats this process for each view. In conventional energy integrating type detector, the energy corresponding to the charges accumulated during one view period is output for each view and each channel. For example, as shown in (a) of FIG. 5, the detector unit of channel m outputs the energy E (n) corresponding to the charges accumulated during view (n) and the energy E (n+1) corresponding to the charges accumulated during view (n+1) sequentially for each view.

Meanwhile, the parts (b) to (f) of FIG. 5 are timing charts corresponding to the operation of the present embodiment. The part (b) of FIG. 5 schematically illustrates the waveform of the signal output from the detector unit 12a of a certain channel, for example, channel m (chm). The detector unit 12a in the present embodiment is also configured as an energy integrating type detector, but the charges stored in the detector unit 12a is not reset by a view trigger as in the conventional method, but by a trigger signal output from the comparator 181 provided in the rear stage of the detector unit 12a.

The part (c) of FIG. 5 shows the trigger signal used to reset the integrator 121. The trigger signal is output from the comparator 181. The comparator 181 compares the threshold E0 corresponding to a predetermined energy with the output signal of the detector unit 12a, and when the output signal of the detector unit 12a exceeds the threshold E0, the trigger signal is generated as shown in (c) of FIG. 5. As a result, the waveform of the output signal of the detector unit 12a becomes zero at the timing of the trigger signal, monotonically increases thereafter, and returns to zero when accumulated charges reaches threshold E0, as shown in (b) of FIG. 5.

When the intensity of the X-rays input to the detector unit 12a is high, the incremental rate of the charge accumulated in the detector unit 12al is large, and thus, the interval between trigger signals becomes short. Conversely, when the intensity of the X-rays input to the detector unit 12a is small, the incremental rate of the charge accumulated in the integrator 121 is small, and as a result, the interval between trigger signals becomes longer. In this way, the X-ray CT apparatus 1 of the present embodiment has a configuration that makes it possible to evaluate the intensity of the X-ray input to the detector unit 12a by replacing it with the interval of the trigger signal.

The trigger signal shown in (c) of FIG. 5 is input to the TDC 182, and the input time of the trigger signal is converted into time data as digital data by the TDC 182. The clock signal and view trigger shown in (d) of FIG. 5 are also input to the TDC 182. Inside the TDC 182, the time corresponding to each clock signal is counted up sequentially from time t1 to time tN at which a reset by the view trigger will be made. Because of the reset by the view trigger at time tN, the size of the time data can be limited, and the data width (number of bits) of the time data can be limited to about 10 bits, for example.

The part (e) of FIG. 5 shows the event occurrence status. In (e) of FIG. 5, As mentioned above, an event according to the present embodiment is an event that indicates that the charges accumulated in each of the detector units 12_a_ has reached a predetermined threshold. In (e) of FIG. 5, the occurrence of an event is indicated by "1" and the non-occurrence of an event is indicated by "0".

As mentioned above, the TDC 182 determines that an event has occurred when the trigger signal from the comparator 181 is input. The TDC 182 then generates the combination of the time data corresponding to the time of the input trigger signal and the identification information of the channel on which the event occurred as event data.

The part (f) of FIG. 5 shows an example of event data generated by the TDC 182. Each time an event occurs, the TDC 182 sequentially generates event data, which is a combination of the channel number on which the event occurred and the time at which the event occurred, such as (ch3, t2), (ch3, t4), (ch3, t8), and the like.

Although in parts (a) to (f) of FIG. 5, only two views, view (n) and view(n+1), are shown, but in reality, event data corresponding to multiple views of one or more rotations are generated.

The event data generated by the TDC 182 for each channel is sent to the event generation circuit 183. The event generation circuit 183 aggregates the event data sent from each channel to generate aggregated event data.

FIG. 6 is a diagram explaining an example of the aggregated event data. The aggregated event data is a set of event data that aggregates event data of each channel such as (ch3, t2), (ch3, t4), (ch3, t8), and the like, for all channels and all views. In the notation for aggregated event data shown in FIG. 6, the channel numbers of the detector unit 12_a_ are arranged horizontally, and the view numbers and the time in the view are arranged vertically. In FIG. 6, only two views, view(n) and view(n+1), are arranged in the vertical direction, but in reality, the multiple views corresponding to one or more rotations and the time in the view are arranged.

In the notation shown in FIG. 6, among the cells defined by channel number in the horizontal direction and time in the vertical direction, the cell indicated by "1" indicates that the event occurred at the corresponding channel number and corresponding time. Therefore, such cell means that there is event data consisting of a combination of the corresponding channel number and the corresponding time data.

Meanwhile, a cell indicated by "0" indicates that no event occurred at the time corresponding to the corresponding channel number. Therefore, such cell means that no event data exists for the corresponding channel number and the corresponding time data.

Returning to FIG. 3, in step ST70, the event data for transmission is generated such that the event data are maintained as it is for the first path that requires a high view rate, while the event data for the other second paths are aggregated.

Figure 7:
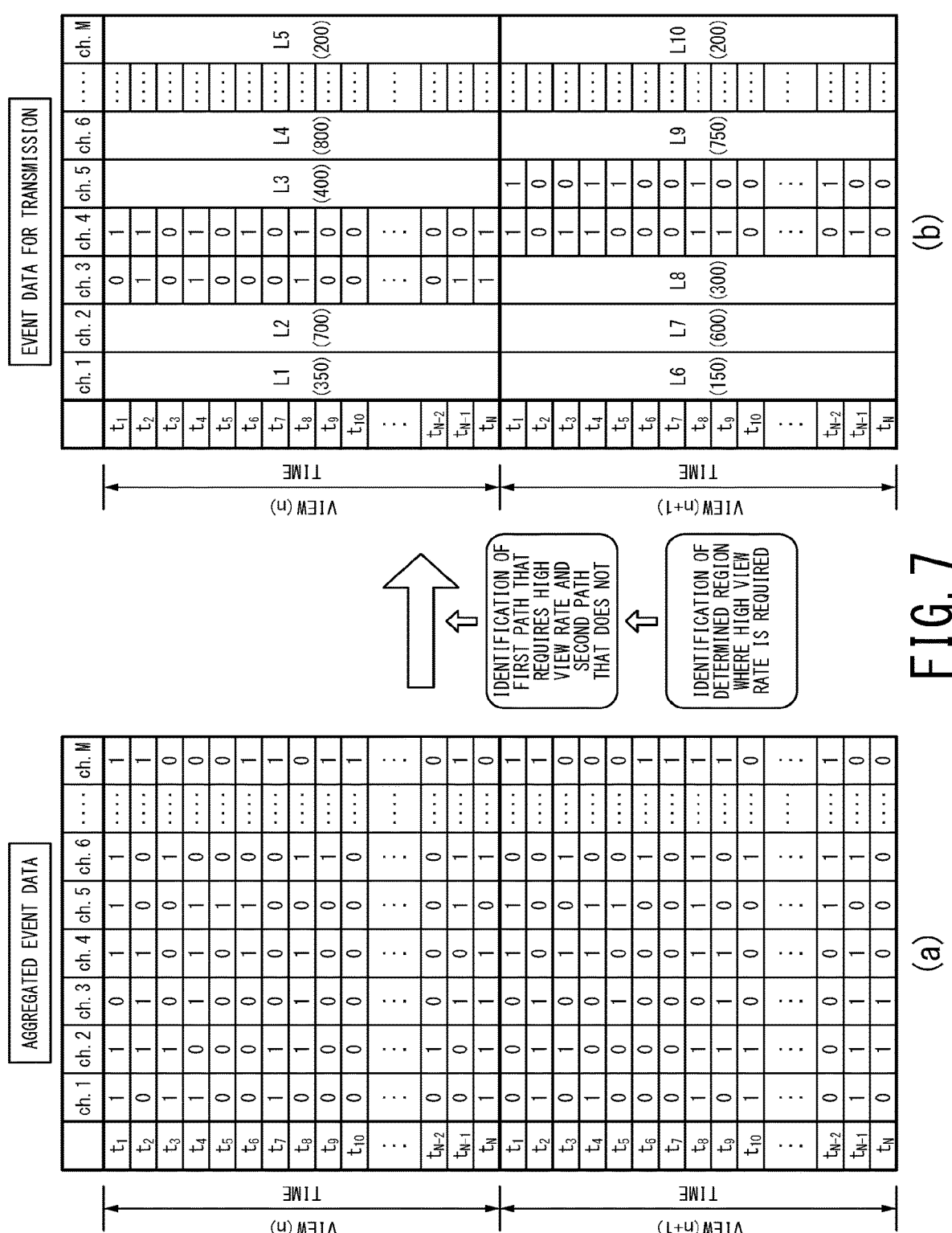
FIG. 7 is a diagram showing an example of a process of generating event data for transmission from aggregated event data.

FIG. 7 is a diagram showing an example of a process of step ST70. The left side of FIG. 7 is the same as FIG. 6 and shows the aggregated event data generated in step ST60. The right side of FIG. 7 shows an example of the event data for transmission generated from the aggregated event data by the process of step ST70.

As mentioned above, the cell indicated by "1" in the aggregated event data shown on the left side of FIG. 7 means that there is event data consisting of a combination of the corresponding channel number and the corresponding time data. Therefore, the entire aggregated event data will contain event data for number of events represented by "1", which is a large amount of data that is not negligible from the data transfer perspective.

Therefore, in step ST70, the data volume of the aggregated event data is reduced based on the information on the first and second paths identified in step ST30. The process in step ST70 is performed by the transmission data generation circuit 184 of the DAS 18.

Specifically, as described above, the event data corresponding to the first path is the first event data where the frequency of event occurrence is maintained at the first view rate. On the other hand, as the event data for the second path, the second event data is generated by aggregating event occurrences and reducing the frequency of event occurrences such that the frequency of event occurrence after aggregation is at a second view rate lower than the first view rate. Specifically, the number of events in the event data corresponding to the second path is aggregated for each view, and the aggregated number of events is used as the second event data.

For example, in the example shown on the right side of FIG. 7, in view(n), the paths leading to each detector unit 12_a_ of channel 3 and channel 4 correspond to the first path, and the other paths correspond to the second path. In view (n+1), the path leading to each detector unit 12_a_ of channel 4 and channel 5 corresponds to the first path, and the other paths correspond to the second path.

As to the second path, the total number of events itself is used as the second event data, such as L1 (350), L2 (700), L3 (400), and the like. For example, when the total number of times N in a view is 1000, and the number of times an event has occurred, i.e., the total number of cells showing "1" in the view, is 350, 700, 400, etc., the number of event occurrence itself, such as 350, 700, 400, etc., is applied as the second event data. As a result, the amount of data in the event data for transmission is greatly reduced.

In step ST80 of FIG. 3, the event data for transmission generated in step ST70 is transferred to the console device 40 via the gantry base 19, which is a fixed unit.

The X-ray CT apparatus 1 has a rotating casing housed in the rotating frame 13 and a fixed casing housed in the gantry base 19, which is a fixed unit, or in the console device 40. The data transmission path between the rotating casing and the fixed casing includes slip rings and non-contact optical transmission paths. Therefore, the amount of data transmission is limited and the transmission path is relatively narrow.

Generally, the amount of data increases as the view rate is increased. In the embodiment of the X-ray CT apparatus 1, the transmission data generation circuit 184, which reduces the amount of data of the aggregated event data, is provided in the housing of DAS 18, which is one of the rotating casing. As a result, data transmission over a narrow transmission path from the DAS 18 to the console device 40, which performs the reconstruction process, is made possible.

Next, in step ST90 of FIG. 3, based on the event data for transmission, the first projection data that is up-sampled above the normal spatial resolution and the second projection data with the normal spatial resolution are generated. More specifically, for the first event data among the event data for transmission, the energy corresponding to the threshold is divided by the interval between two adjacent time data to generate the first projection data of the first path that passes through the determined region. The first projection data is the projection data upsampled to the first view rate adapted to the minute angle described above.

On the other hand, for the second event data among the event data for transmission, the second projection data with the aforementioned second view rate corresponding to the normal view described above is generated based on the integrated value of the number of events in each view. Step ST90 is performed by the projection data calculation function F02.

Figures 8A, 8B:
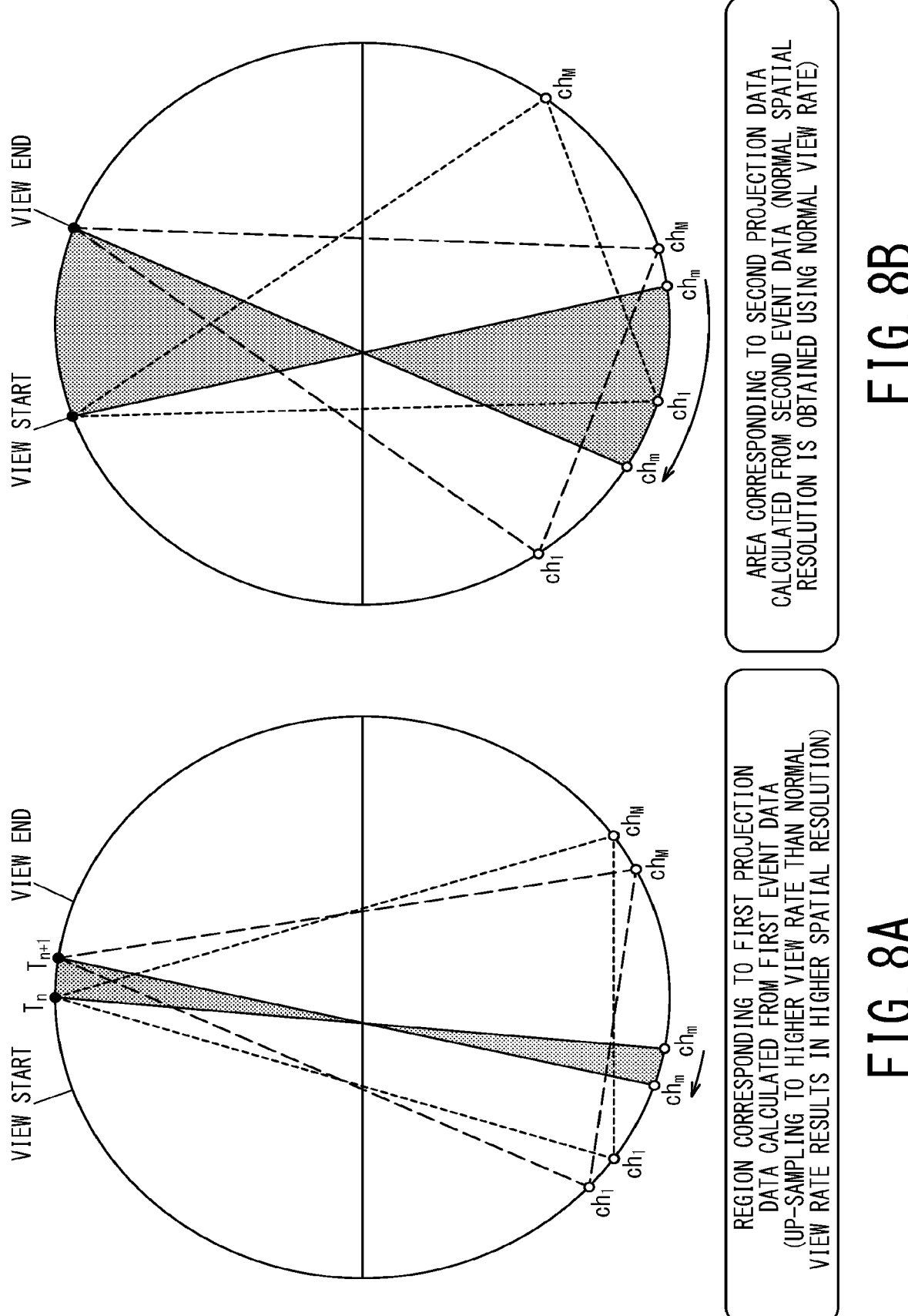
FIG. 8A is a diagram showing a spatial region corresponding to the first projection data calculated from the first event data with hatching.
FIG. 8B is a diagram showing a spatial region corresponding to the second projection data calculated from the second event data by hatching.
Figure 9:
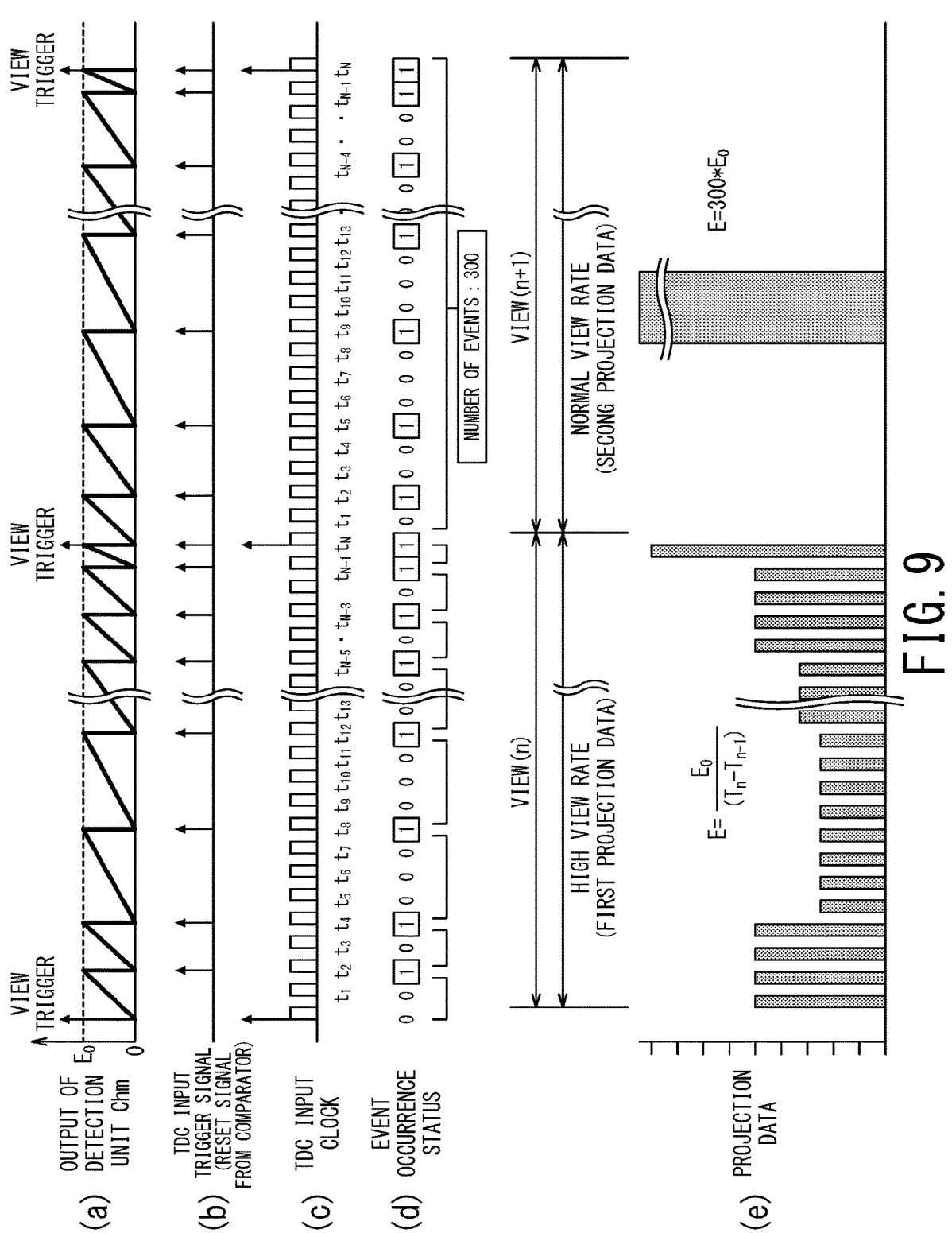
FIG. 9 is a second diagram illustrating an example of processing for generating the first and second projection data from event data for transmission.

FIG. 8 and FIG. 9 show a processing example of step ST90. FIG. 8A shows the spatial region corresponding to the first projection data calculated from the first event data by hatching. In FIG. 8A, the hatching shows the spatial region focused on one specific channel (ch m) among the multiple channels.

In FIG. 8A, the angular range from "VIEW START" to "VIEW END" in a clockwise direction is the interval of the normal view (see FIG. 8B). In contrast, the spatial region corresponding to the first projection data indicates that the normal view interval is upsampled and a higher spatial resolution than above normal becomes available.

As mentioned above, the value of the first projection data (E) can be calculated, for example, by dividing the energy (E0) corresponding to the threshold by the interval between two adjacent time data. Specifically, it can be calculated by the following equation.

$$E = E0/(Tn+1 - Tn) \qquad \text{(Eq. 1)}$$

Where Tn+1 and Tn are the time data when the event occurred, each of which is output from the TDC 182, and (Tn+1−Tn) indicates the interval between the occurrence times of adjacent events.

FIG. 8B shows the spatial region corresponding to the second projection data calculated from the second event data by hatching. In FIG. 8B, as in FIG. 8A, the spatial region focused on one specific detector unit 12*a* (ch m) among the multiple detector units 12*a* is shown by hatching.

As shown in FIG. 8B, the second projection data has the normal view rate, and the spatial region corresponding to the second projection data has the normal spatial resolution.

As mentioned above, the value of the second projection data (E) can be calculated based on the integration of the number of events within a view. For example, when an event occurs L times within a view, the value of the second projection data (E) can be calculated using the following equation.

$$E = L * E0 \qquad \text{(Eq. 2)}$$

FIG. 8A and FIG. 8B show the view interval (interval from "VIEW START" to "VIEW END") at an extremely larger scale than the actual view interval of the X-ray CT apparatus in operation, in order to facilitate understanding of the technical effect obtained by the X-ray CT apparatus 1 according to the embodiment. In an actual X-ray CT apparatus, the number of views in one rotation can be several hundred or more. However, in order to simplify the explanation, even when the number of views is assumed to be 360, which is less than the actual number, the view interval from "VIEW START" to "VIEW END" is deemed as 1°.

Meanwhile, in the first event data, it is not impossible to divide one view into 1000 (t1 to tN: N=1000), for example, as illustrated in FIG. 6 and FIG. 7. In this case, the first projection data will have a spatial resolution equivalent to 0.001° as the highest spatial resolution.

FIG. 9 shows the processing example of step ST90 on the time axis. The parts (a) through (d) of FIG. 9 are the same as the parts (b) through (e) of FIG. 5, and the explanation is omitted. The first half of (e) of FIG. 5 illustrates the first projection data corresponding to view (n), and the second half of (e) of FIG. 5 illustrates the second projection data corresponding to view (n+1).

As mentioned above, the first projection data is generated as projection data divided into multiple views. That is, the first projection data is generated as projection data in which one view is upsampled into multiple views. Specifically, the first projection data is calculated based on (Eq. 1) described above for each occurrence of an event. The time between the first event and the second event immediately following the first event can be supplemented by the value of the first projection data calculated for the second event, for example.

The second projection data, on the other hand, is generated as projection data with a single, normal view rate in the view. Specifically, the second projection data is calculated based on (Eq. 2) described above. For example, when the number of events in view (n+1) is 300, the second projection data is calculated as E=300*E0.

As can be seen from (a) to (e) of FIG. 9, the spatial resolution of the first projection data can be changed by changing the clock frequency of the clock signal input to the TDC 182 and also by changing the threshold value input to the comparator 181.

Returning to FIG. 3, in step ST100, a two dimensional or three dimensional CT image is generated by applying reconstruction processing using the inverse projection method or the like to the first projection data and the second projection data described above.

The combination of the event generation circuit, transmission data generation circuit, path determination function, and projection data calculation function in the description of the embodiments is an example of a projection data generation unit in the claims. The combination of the detector and the time data generation circuit in the description of the embodiments is an example of a radiation detecting apparatus in the claims.

According to at least one of the above-described embodiments, the view rate can be changed according to the area in the FOV of the object.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:

an X-ray tube emitting X-rays;

an energy integrating type detector having a plurality of detector units arrayed in a channel direction that accumulate electric charges corresponding to X-rays transmitted through an object;

a time data generation circuit configured to generate time data at a timing when the electric charges accumulated in the detector reach a predetermined threshold; and a projection data generation circuitry configured to generate projection data using the time data and energy corresponding to the threshold, wherein the time data generation circuit is further configured to generate the time data for each of the plurality of the detector units; and the projection data generation circuitry includes an event generation circuit configured to generate event data, which is associated with an event indicating that the electric charges accumulated in a detector unit of the detector units reaches the predetermined threshold, and is associated with the time data indicating a time when the event occurred and identification information of the detector unit in which the event occurred.

2. The X-ray CT apparatus according to claim 1, wherein the time data generated by the time data generation circuit is associated with a rotation angle of the X-ray tube and the detector.

3. The X-ray CT apparatus according to claim 1, wherein the projection data generation circuitry is further configured to generate projection data with different view rates according to a position in a field of view (FOV) of the object.

4. The X-ray CT apparatus according to claim 1, wherein the time data generation circuit includes:

a comparator that generates a trigger signal to reset the electric charges stored in the detector when the electric charge stored in the detector exceeds said threshold; and a TDC (Time to Digital Converter) that is input with the trigger signal generated by the comparator and generates the time data at the timing when the trigger signal is input.

5. The X-ray CT apparatus according to claim 1, wherein the projection data generation unit further includes:

processing circuitry configured to identify, while the X-ray tube and the detector rotate, a first path in which the X-ray emitted from the X-ray tube passes through a determined region set in a field of view (FOV) of the object and is incident on the detector, and a second path in which the X-ray to is incident on the detector without passing through the determined region; and a transmission data generation circuit configured to a generate first event data such that a frequency of occurrence of the event is maintained at a first view rate for event data corresponding to the first path, aggregate occurrence of the events and generates second event data such that a frequency of occurrence of events after aggregation is at a second view rate lower than the first view rate for event data corresponding to the second path, and combine the first event data with the second event data to generate event data for transmission.

6. The X-ray CT apparatus according to claim 5, wherein:

the first view rate of the first event data is a view rate having a resolution corresponding to a minute angle in which a predetermined view interval is divided into multiple views; and the second view rate of the second event data is a view rate that is reduced from the first view rate by accumulating, view by view, a number of events in the event data corresponding to the second path.

7. The X-ray CT apparatus according to claim 6, wherein the processing circuitry of the projection data generation unit is further configured to:

with respect to the first event data, by dividing an energy corresponding to the threshold by an interval between time data corresponding to the occurrence times of two adjacent events, generate first projection data by upsampling the projection data that corresponds to the first path through the determined region to the first view rate corresponding to the minute angle; and with respect to the second event data, generate second projection data having the second view rate corresponding to the view interval, based on accumulated number of events.

8. The X-ray CT apparatus according to claim 7, further comprising a rotating frame and a fixed frame, wherein the transmission data generation circuit is housed in the rotating frame and the processing circuitry is housed in the fixed frame, and the event data for transmission is transmitted via a transmission path between the rotating frame and said fixed frame.

9. The X-ray CT apparatus according to claim 7, wherein the processing circuitry is further configured to generate a tomographic image by reconstruction processing using the first projection data and the second projection data.

10. The X-ray CT apparatus according to claim 5, wherein the determined region set within the FOV is at least one of (a) a peripheral region of the FOV, (b) a region with microstructure that is determined, based on a preliminary imaging image of the object, to be prone to partial volume effects, and (c) a region in a vicinity of dense material that is determined, based on a preliminary imaging image of the object, to be prone to artifacts.

11. A radiation detecting apparatus, comprising:

an energy integrating type detector having a plurality of detector units arrayed in a channel direction that accumulate electric charges corresponding to radiation transmitted through an object; and a time data generation circuit generating time data at a timing when the electric charges accumulated in the detector reach a predetermined threshold, wherein the time data generation circuit generates the time data for each of the plurality of the detector units.

12. A data processing method for an X-ray CT apparatus including at least an X-ray tube emitting X-rays and an energy integrating type detector having a plurality of detector units arrayed in a channel direction that accumulate electric charges corresponding to X-rays transmitted through an object, the method comprising:

generating time data at a timing when the electric charges accumulated in the detector reach a predetermined threshold;

generating projection data using the time data and energy corresponding to the threshold;

generating the time data for each of the plurality of the detector units; and generating event data, which is associated with an event indicating that the electric charges accumulated in a detector unit of the detector units reaches the predetermined threshold, and is associated with the time data indicating a time when the event occurred and identification information of the detector unit in which the event occurred.

* * * * *